(12) United States Patent
Organ et al.

(10) Patent No.: US 7,390,513 B2
(45) Date of Patent: Jun. 24, 2008

(54) FOOD SUPPLEMENT FORMULATION

(75) Inventors: Eric J. Organ, Kinnelon, NJ (US); Denise L. Organ, Kinnelon, NJ (US)

(73) Assignee: D & E Pharmaceuticals, Bloomingdale, NJ (US)

( * ) Notice: Subject to any disclaimer, the term of this patent is extended or adjusted under 35 U.S.C. 154(b) by 516 days.

(21) Appl. No.: 10/864,987

(22) Filed: Jun. 10, 2004

(65) Prior Publication Data
US 2005/0276870 A1 Dec. 15, 2005

(51) Int. Cl.
*A61K 36/81* (2006.01)
*C07C 229/00* (2006.01)

(52) U.S. Cl. .................... 424/729; 424/760; 562/445

(58) Field of Classification Search .................. None
See application file for complete search history.

(56) References Cited

U.S. PATENT DOCUMENTS 6,693,104 B2 * 2/2004 Lee et al. ............... 514/263.34

2003/0104076 A1 * 6/2003 Berkulin et al. ............. 424/725
2003/0181414 A1 * 9/2003 Valducci et al. ............... 514/45

OTHER PUBLICATIONS http://www.tropilab.com/capsicum.html, 1 pg.*
https://www.drugdigest.org/DD/DVH/HerbsWho/0,3923,4095%7CCapsicum+frutescens,00.html, 1 pg.*
http://www.gardenguides.com/plants/info/herbs/cayenne.asp), 2 pgs.*
http://web.archive.org/web/20020821220539/http://www.whfoods.com/genpage.php?tname=foodspice&dbid=140.*
http://news.bbc.co.uk/2/hi/health/3125469.stm.*
Yamada et al., Production f L-Phenylalanine from trans-Cinnamic Acid with Rhodotorula glutinis Containing L-Phenylalanine Ammonia-Lyase Activity, 1981, Applied and Environmental Microbiology, vol. 42, pp. 773-778.*

* cited by examiner

*Primary Examiner*—Susan Hoffman
*Assistant Examiner*—Catheryne Chen
(74) *Attorney, Agent, or Firm*—Fraser Clemens Martin & Miller LLC; Donald R. Fraser

(57) ABSTRACT

A food supplement formulation comprises theobromine, L-phenylalanine, nicotinamide adenine dinucleotide, cayenne pepper, and green tea.

19 Claims, No Drawings

FOOD SUPPLEMENT FORMULATION

FIELD OF THE INVENTION

The present invention relates generally to a food supplement formulation. More particularly, the invention is directed to a food supplement formulation containing natural ingredients whose combination may assist in promoting the energy level of the human body.

BACKGROUND OF THE INVENTION

Natural compounds, including herbal formulations, can provide a healthy supplement to the daily human diet. Certain natural compounds are useful for proper functioning of the human body and for assuring high energy levels, but are not contained in appropriate quantities in the daily diets of many people. It is know to use ephedra-based products to boost energy levels, but such products have recently been spurned by the public as unsafe and ineffective.

It would be desirable to prepare an ephedra-free food supplement formulation that might promote generally good health and simultaneously boost one's energy level.

SUMMARY OF THE INVENTION

Accordant with the present invention, there has surprisingly been discovered a food supplement formulation, comprising: theobromine; L-phenylalanine; nicotinamide adenine dinucleotide; cayenne pepper; and green tea.

The food supplement formulation according to the present invention is particularly useful as a human dietary supplement.

DETAILED DESCRIPTION OF EXEMPLARY EMBODIMENTS OF THE INVENTION

The present invention is directed to a food supplement formulation, comprising theobromine, L-phenylalanine, nicotinamide adenine dinucleotide, cayenne pepper, and green tea.

Theobromine is a well-known alkaloid, of the class of molecules known as methylxanthines. Theobromine is the primary methylxanthine in products of the cocoa tree. Theobromine is useful as a mild stimulant, and for relaxing the smooth muscles of the bronchi and lungs. Theobromine may be present in the inventive formulation at a concentration ranging from about 0.1 to about 1 weight percent. Preferably, the concentration of theobromine is about 0.25 weight percent.

L-phenylalanine is a well-known protein amino acid, derived principally from animal and vegetable proteins. L-phenylalanine is known to be useful for elevating the norepinephrine and dopamine levels in the human brain. L-phenylalanine may be present in the inventive formulation at a concentration ranging from about 20 to about 80 weight percent. Preferably, the concentration of L-phenylalanine is about 49.14 weight percent.

Nicotinamide adenine dinucleotide is a well-known naturally occurring coenzyme form of vitamin B3. Nicotinamide adenine dinucleotide is known to promote improved physical energy and mental alertness, and may enhance the production of essential neurotransmitters in the human brain. Nicotinamide adenine dinucleotide may be present in the inventive formulation at a concentration ranging from about 0.1 to about 1 weight percent. Preferably, the concentration of nicotinamide adenine dinucleotide is about 0.25 weight percent.

Cayenne pepper is a well-known herbal compound, known to be useful for activating human body thermogenesis and for decreasing the human appetite. Cayenne pepper may be present in the inventive formulation at a concentration ranging from about 0.5 to about 5 weight percent. Preferably, the concentration of cayenne pepper is about 1.22 weight percent.

Green tea is a well-known herbal compound, known to be useful for increasing human body energy expenditure, for oxidizing human body fat, and for the activation of thermogenesis. Green tea may be present in the inventive formulation at a concentration ranging from about 20 to about 80 weight percent. Preferably, the concentration of green tea is about 49.14 weight percent.

The aforementioned ingredients may be dried, ground, and mixed together by conventional techniques. Thereafter, the powder mixture may be pressed and formed into tablets, or placed in gelatin capsules, for oral administration. The inventive food supplement formulation may additionally contain conventional, non-active adjuvants such as, for examples, fillers and extenders. Conveniently, the inventive food supplement formulation may be taken orally at a dosage rate ranging from about 200 to about 3,000 milligrams per day. Preferably, the dosage rate is about 800 milligrams per day.

The invention is more easily comprehended by reference to the specific embodiments recited hereinabove, which are representative of the invention. It must be understood, however, that the recited embodiments are provided for the purpose of illustration, and that the invention may be practiced otherwise than as specifically illustrated without departing form its spirit and scope.

What is claimed is:

1. A food supplement formulation, consisting essentially of:
   theobromine;
   L-phenylalanine;
   nicotinamide adenine dinucleotide;
   cayenne pepper; and
   green tea.

2. The food supplement formulation according to claim 1, wherein the concentration of theobromine ranges from about 0.1 to about 1 weight percent.

3. The food supplement formulation according to claim 1, wherein the concentration of L-phenylalanine ranges from about 20 to about 80 weight percent.

4. The food supplement formulation according to claim 1, wherein the concentration of nicotinamide adenine dinucleotide ranges from about 0.1 to about 1 weight percent.

5. The food supplement formulation according to claim 1, wherein the concentration of cayenne pepper ranges from about 0.5 to about 5 weight percent.

6. The food supplement formulation according to claim 1, wherein the concentration of green tea ranges form about 20 to about 80 weight percent.

7. The food supplement formulation according to claim 1, wherein the concentration of theobromine is about 0.25 weight percent.

8. The food supplement formulation according to claim 1, wherein the concentration of L-phenylalanine is about 49.14 weight percent.

9. The food supplement formulation according to claim 1, wherein the concentration of nicotinamide adenine dinucleotide is about 0.25 weight percent.

10. The food supplement formulation according to claim 1, wherein the concentration of cayenne pepper is about 1.22 weight percent.

11. The food supplement formulation according to claim 1, wherein the concentration of green tea is about 49.14 weight percent.

12. A food supplement formulation, consisting essentially of:
   from about 0.1 to about 1 weight percent theobromine;
   from about 20 to about 80 weight percent L-phenylalanine;
   from about 0.1 to about 1 weight percent nicotinamide adenine dinucleotide;
   from about 0.5 to about 5 weight percent cayenne pepper; and
   from about 20 to about 80 weight percent green tea.

13. The food supplement formulation according to claim 12, wherein the concentration of theobromine is about 0.25 weight percent.

14. The food supplement formulation according to claim 12, wherein the concentration of L-phenylalanine is about 49.14 weight percent.

15. The food supplement formulation according to claim 12, wherein the concentration of nicotinamide adenine dinucleotide is about 0.25 weight percent.

16. The food supplement formulation according to claim 12, wherein the concentration of cayenne pepper is about 1.22 weight percent.

17. The food supplement formulation according to claim 12, wherein the concentration of green tea is about 49.14 weight percent.

18. A food supplement formulation, consisting essentially of:
   about 0.25 weight percent theobromine;
   about 49.14 weight percent L-phenylalanine;
   about 0.25 weight percent nicotinamide adenine dinucleotide;
   about 1.22 weight percent cayenne pepper; and
   about 49.14 weight percent green tea.

19. A food supplement formulation, consisting of:
   theobromine;
   L-phenylalanine;
   nicotinamide adenine dinucleotide;
   cayenne pepper; and
   green tea.

* * * * *